United States Patent [19]
Snider et al.

[11] Patent Number: 5,487,727
[45] Date of Patent: Jan. 30, 1996

[54] METHOD OF IMPLANTING AN INTRAVASCULAR MEMBRANE LUNG

[75] Inventors: Michael T. Snider, Hershey; Kane M. High, Middletown, both of Pa.; Georg Panol, Warwick, R.I.; James Ultman, State College, Pa.; Russell B. Richard, Hershey, Pa.; John K. Stene, Hummelstown, Pa.; Garfield B. Russell, Palmyra, Pa.

[73] Assignee: The Penn State Research Foundation, University Park, Pa.

[21] Appl. No.: 232,788

[22] Filed: Apr. 22, 1994

Related U.S. Application Data

[62] Division of Ser. No. 817,173, Jan. 6, 1992, Pat. No. 5,336,164.

[51] Int. Cl.⁶ .......................... A61M 37/00; A61M 31/00
[52] U.S. Cl. .......................... 604/49; 604/26; 128/DIG. 3
[58] Field of Search .......................... 604/4–6, 26, 49; 128/DIG. 3; 623/12

[56] References Cited

U.S. PATENT DOCUMENTS

| | | | |
|---|---|---|---|
| 4,583,969 | 4/1986 | Mortensen | 604/4 |
| 4,631,053 | 12/1986 | Taheri | 128/DIG. 3 |
| 4,850,958 | 7/1989 | Berry et al. | 604/26 |
| 4,889,137 | 12/1989 | Kolobow | 606/191 |
| 4,950,224 | 8/1990 | Gorsuch et al. | 604/6 |
| 5,098,376 | 3/1992 | Berry et al. | 604/26 |
| 5,376,069 | 12/1994 | Hattler | 604/26 |

Primary Examiner—Mary Beth O. Jones
Assistant Examiner—Dennis Ruhl
Attorney, Agent, or Firm—Thomas J. Monahan

[57] ABSTRACT

An intravascular membrane lung is adapted for percutaneous venous insertion into a living body and comprises an elongated multi lumen catheter and elongated gas exchange members in the form of a large number of microporous fibers tethered at one end to the catheter and extending away from the catheter in all directions. The microporous fibers are in communication with the lumina of the catheter which includes one conduit for delivery of 100% oxygen to the fibers and another conduit for flushing away carbon dioxide from the fibers. The catheter extends between a proximal end and a distal end being a leading end for insertion into the body. The distal end includes a selectively inflatable balloon having an enlarged size larger than a nominal transverse dimension of said catheter and smaller than the inner nominal dimensions of any of the body cavities into which it extends. Upon insertion into the femoral vein, the blood flowing back to the natural lungs of the body propel the catheter and its attached microporous fibers through the inferior vena cava, then into and through the right ventricle, then into and through the pulmonary artery. Another lumen of the catheter serves to receive a fiberoptic bundle to monitor oxygenation of the blood which has passed over the device and still another lumen is provided for sampling blood at the tip of the catheter.

7 Claims, 11 Drawing Sheets

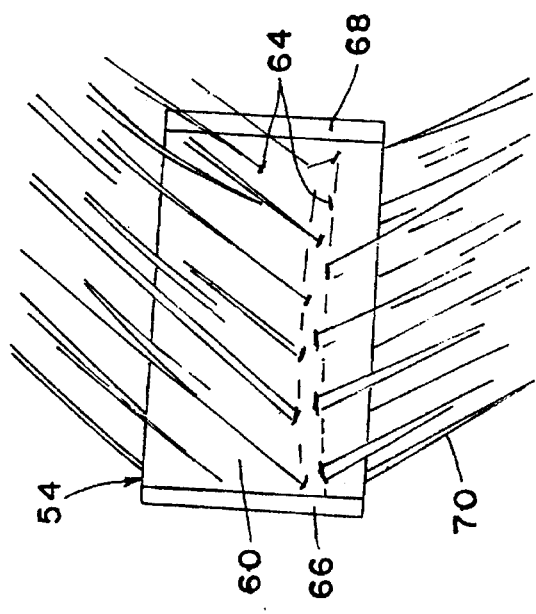
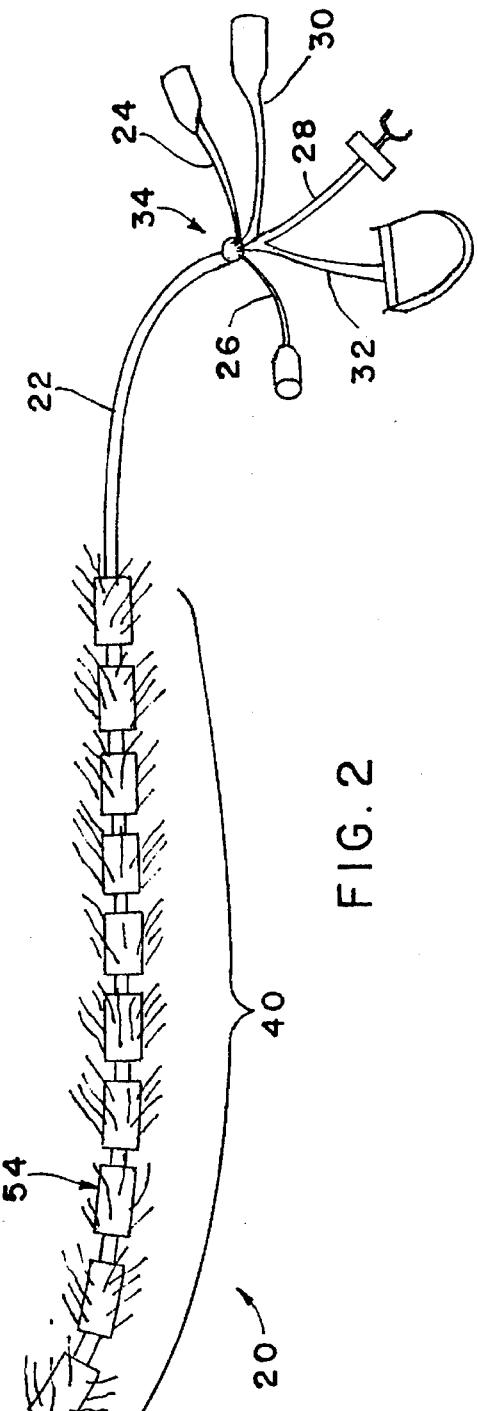
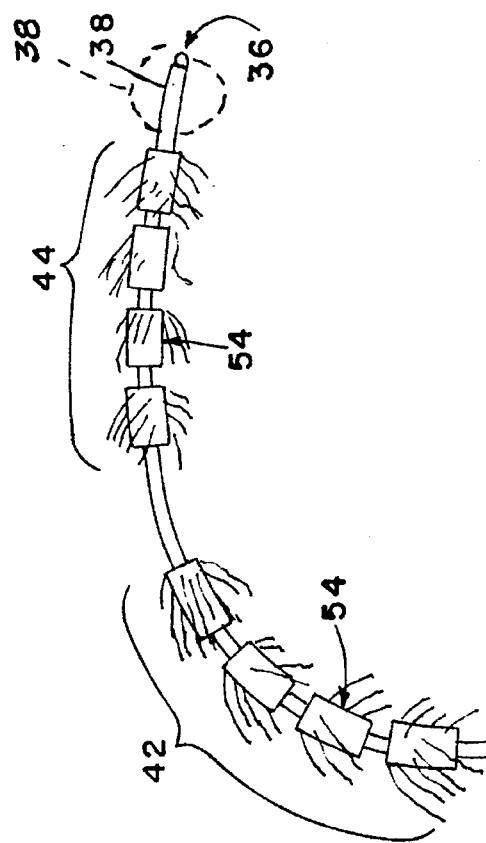
FIG. 7
FIG. 2

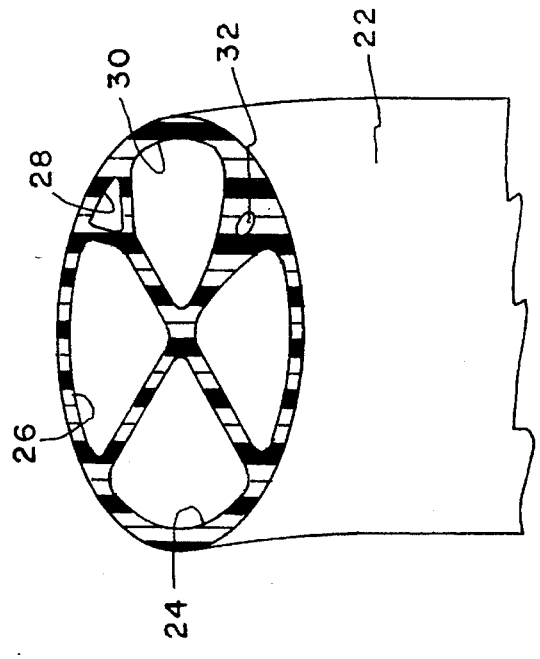
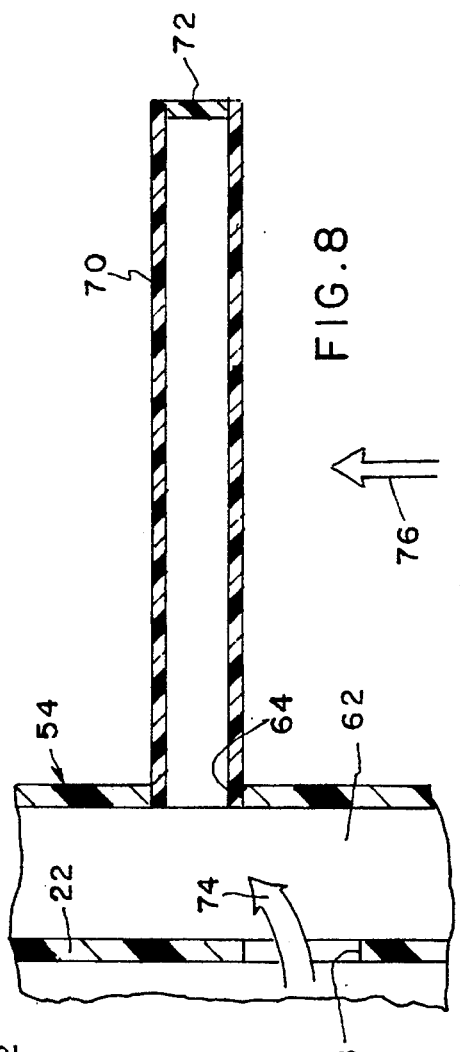
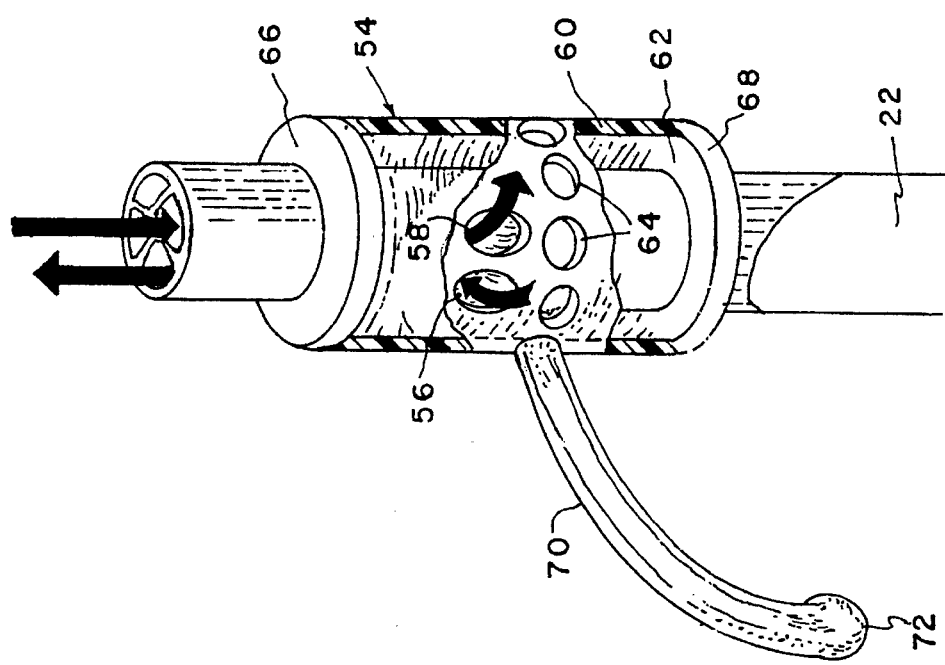
FIG. 3
FIG. 8
FIG. 6

METHOD OF IMPLANTING AN INTRAVASCULAR MEMBRANE LUNG

This is a divisional of application Ser. No. 07/817,173 filed on Jan. 6, 1992 now U.S. Pat. No. 5,336,164 Mar. 13, 1995.

BACKGROUND OF THE INVENTION

1. Field of the Invention

The present invention relates generally to artificial lungs and, more particularly, to a new configuration intravascular membrane lung which, after percutaneous insertion, will be capable of exchanging the entire basal oxygen consumption and carbon dioxide production of an adult man or woman.

2. Description of the Prior Art

Intravascular membrane lungs have notable benefits. They do not require blood pumps, nor lung resection. In addition, the intravascular membrane lung has the advantage that the skin and circulation need only be violated at one location for its insertion at a peripheral site. This may lessen the risk of infection. However, known devices also have significant shortcomings. Unfortunately, the largest model of the most advanced current design, the intravenous oxygenator (IVOX), disclosed in U.S. Pat. No. 4,583,969 to Mortensen, can at best exchange only approximately 40% of basal metabolic needs of the adult patient. Most current designs of intravascular membrane lungs cannot be inserted percutaneously, and require cutdown on the vessel prior to insertion. Any device which is to have widespread use must be capable of rapid insertion using something similar to the well known Seldinger technique. Membrane lungs mounted paracorporeally outside the chest wall, with or without a blood pump, is actually extracorporeal membrane oxygenation with a special cannulation site. Also, a device with a single insertion site has little effect on the turning of a patient for chest physical therapy as would a paracorporeal mounted lung with two cannulae protruding from the chest.

The physical/chemical properties of the oxygen dissociation curve presented in FIG. 1 shows the limit of the amount of oxygen which can be transferred into a given blood flow stream by an intravascular lung. Even if an intravascular lung had no convective or diffusion limitations to oxygen transfer, the maximum oxygen transfer would still be limited by the blood flow rate across the device and the oxygen saturation of the input blood. This occurs because the oxygen saturation curve constrains the oxygen content of the blood exiting the device. Hence, the maximum oxygen transport is limited to the product of the difference between 100% flow rate over the device, and the oxygen carrying capacity of the blood. A gas exchanger such as the IVOX of the Mortensen patent which primarily processes inferior vena caval blood, or approximately half of the cardiac output, can only expect at best to transfer a maximum of 40-50% of basal oxygen requirements.

On the other hand, if the gas exchange surface or the membrane lung were placed not only in the inferior vena cava, but also extended into the right ventricle and the pulmonary artery, the low saturation blood returning from the coronary sinus as well as that of the superior vena cava could be oxygenated. Also, the opening and closure of the tricuspid valve, the contraction of the right ventricle and the opening and closing of the pulmonic valve produce intravascular secondary blood flows. This may reduce the resistance to oxygen transfer of the blood boundary layer adjacent to the membrane lung gas exchange surface. In addition, other intravascular lung designs have shown that it is difficult to achieve a closer packing of fibers in the inferior vena cava than the current IVOX has without interfering with venous return.

In the Mortensen, or IVOX, device, noted above, hollow fibers of 25 to 65 centimeters in length are mounted and extend between two spaced apart manifolds. As mentioned, the device is intended to be placed only in the vena cava. Oxygen is passed through the hollow fibers, and gas exchange occurs through the permeable membrane with the blood of the vena cava. In an initial design, gas entered through a cannula in the femoral vein and exited through a cannula in the right internal jugular vein. In a later design, a concentric double catheter allows gas flow to occur through a single cannula. The device is inserted by surgical isolation of the access vessel and advanced into the vena cava with only the tip of the device lying in the superior vena cava. In this position, most of the surface area of the gas exchange membrane is exposed to blood returning to the right atrium via the vena cava. The gas exhaust limb is open to the atmosphere and the gas supply pressure is kept at less than 15 mm Hg (gauge). Gas flow through the IVOX is provided by supplying gas at atmospheric pressure to the inlet manifold and drawing a partial vacuum at the exhaust manifold. Gas flows up to 3 liters/minute have been obtained. This method of obtaining gas flow has been utilized to reduce the risk of positive pressure within the microporous hollow fibers forcing gas bubbles into the vena cava.

Variations on the Mortensen design are disclosed in U.S. Pat. Nos. 4,986,809 and 4,911,689 to Hattler and 4,850,958 to Berry et al. In the Hattler oxygenator, a plurality of hollow, gas permeable fibers extend from a Y-shaped tubular connector either to a ring or to a tip end, then, in loops, return to the connector. This arrangement is percutanaeously inserted into a vein and, once in place, occupies the superior vena cava, inferior vena cava, right atrium, or some combination of these areas in the patient. The patent explains that the fiber loops can be crimped and/or twisted into a helical arrangement to enhance gas exchange. The Berry et al. apparatus includes a metal rod for structural support of the gas permeable tubes and that apparatus is intended for placement within the venae cavae of a patient.

Also known are lung assist devices such as that disclosed in U.S. Pat. No. 5,037,383 to Vaslef et al. The Vaslef et al device is comprised of short subunits of shorter looped hollow fibers with several subunits placed along a central gas supply and exhaust line. These have been tested in a cylindrical blood flow channel to determine gas exchange parameters and resistance to blood flow. As reported in Vaslef, S. N.; Mockros, L. F.; Anderson, R. W.: "Development of an Intravascular Lung Assist Device"; *Transactions of the American Society of Artificial Internal Organs*; Vol. XXXV:660–664, 1989, up to 100 cc of $CO_2$ and $O_2$ gas exchange were possible with devices with a greater number of fibers but with unacceptable pressure drops across the device of up to 100 mm Hg at 4.7 liters/min.

Still another variation of known oxygenators is that disclosed in U.S. Pat. No. 4,631,053 to Taheri which discloses a disposable device for insertion into the inferior vena cava of a patient. It includes a hollow tubular gas permeable membrane having numerous side branches said in the patent to resemble pine needles on a pine branch. The membrane is mounted on a support wire and is surrounded by a sheath through which blood can flow. The sheath is also secured to the support wire. It is unclear from a study of this patent as to whether the gas permeable membrane or the pine needles themselves provide the major portion of gas exchange. There is no description as to how to optimize either the shape, length or number of fibers to provide gas exchange. Also, the device is located in the lower part of the inferior vena cava and, at best, could only oxygenate and decarbonate blood returning from the lower extremities.

A major problem posed by known artificial lungs using microporous membranes as the gas exchange surface is that they can lose their ability to transfer oxygen and carbon dioxide in as little as four to six hours after the beginning of extracorporeal circulation. This deterioration has been attributed to condensation of water in the gas phase or the transudation of plasma from the blood phase across the microporous membrane phase. In Mottaghy, K.; Oedekoven, B.; Starmans, H.; Muller, B.; Kashefi, A.; Hoffman, B. and Bohm, S.: "Technical Aspects of Plasma Leakage Prevention in Microporous Capillary Membrane Oxygenators"; *Transactions of the American Society of Artificial Internal Organs*; Vol. XXXV:640–643, 1989, Mottaghy et al. reported a method for prolonging the use of microporous hollow fibers by heating of the gas flushing the membrane lung. They postulated that the temperature of the gas passing through the hollow fibers has a significant effect on the cooling and condensation of liquid passing through the micropores. In normal operation the gas is cooler than the blood and thereby cools the water vapor within the gas phase causing condensation and filling of the micropores. The condensed water was further postulated to pull plasma across the microporous membrane by capillary action. By heating the gas to a temperature of about 2° C. greater than blood temperature, use of this type of membrane was extended to a duration of five days without any decrement of gas exchange. This represents a significant step in the quest for developing a successful artificial lung.

Hollow fibers of microporous polypropylene generally of the type disclosed in U.S. Pat. No. 4,770,852 to Takahara et al. have been used as the gas exchange surface in membrane lung gas exchangers designed for short term use during cardiopulmonary bypass for cardiac surgery. These devices have shown excellent gas exchange with little hemolysis or formed element damage. Importantly, the raw microporous surface has a maximal gas exchange which is decreased by coating it with any continuous polymer such as silicone. Recent studies have shown that microporous membranes will not degrade their performance for at least a week if gas heated above the body temperature is used to ventilate the fibers. Finally, polypropylene is capable of covalent heparin bonding via the CARMEDA® Process, a proprietary process licensed to and commercialized by the Cardiopulmonary Division of Medtronic, Inc., of Anaheim, Calif.

As evidenced by the patents, noted above, particularly those to Berry et al., Hatter, Mortensen, and to Vaslef et al, present intravascular lungs which use hollow fibers for gas exchange have these fibers tethered at both ends of their gas conduit catheter. Thus, the gas flushing the catheter sweeps through the lumen of the fibers and convects oxygen to the wall of the fiber for diffusion out while the carbon dioxide, which has diffused in, is convected away. This method of mounting the fibers results in the direction of much of the blood flow being in parallel with the axes of the fibers. In contrast, in the device of the invention, the fibers are tethered at only one end to a catheter while the other ends of the fibers are sealed and float freely generally transversely of the blood stream. In this manner, blood flow occurs transversely of, or across, the axes of the fibers floating in the blood stream. This cross flow arrangement of fibers and blood flow optimizes oxygen transfer. By use of fibers tethered only at one end, diffusion of the oxygen and carbon dioxide along each hollow fiber from the fiber wall to the gas flushing the central catheter becomes a major process in mass transfer which may be augmented by secondary gas flows set up by high frequency oscillations of the supply gas pressure. Such high frequency oscillators are in common use for augmenting gas exchange in the natural lung. The exact mechanism of augmented secondary flow is unknown. However, having a gas with compressable properties will probably allow an augmentation of diffusion down the axis of the fiber.

SUMMARY OF THE INVENTION

It was with knowledge of the foregoing that the present invention was conceived and has now been reduced to practice. The overall objective of the invention is to develop and optimize a new configuration intravascular membrane lung which after percutaneous venous insertion will exchange the entire basal oxygen consumption and carbon dioxide production of an adult man or woman. The gas exchange surface comprises hollow cylindrical fibers of microporous polypropylene which are tethered to a central catheter at only one end while the other end of the fiber floats free in the blood stream. The central catheter contains two lumens for gas flow. One lumen acts as a gas inlet conduit for delivering 100% oxygen to the fibers. The other lumen acts as a gas outlet conduit for flushing away carbon dioxide from the fibers. A fiberoptic bundle monitors oxygenation of the blood which has passed over the device. A lumen is also provided for sampling blood at the tip of the catheter.

This miniaturized membrane lung is inserted percutaneously into the common femoral vein. A balloon at the tip is then inflated and the blood flowing back to the lungs from the peripheral tissues propels the catheter with its fibers through the inferior vena cava, the right ventricle and into the pulmonary artery. Thus, gas exchange fibers are caused to float in the blood at each site. Since deoxygenated blood from the patient's entire circulation passes over portions of the device, complete basal oxygen and carbon dioxide transfer is possible. By coating the device with heparin, the need for an intravenous heparin infusion is minimized which may in turn lessen the risk of hemorrhage from the insertion sites. The optical fibers at the catheter tip allow the effect on mixed venous oxygen saturation to be determined easily. By using optical fibers within the pulmonary artery catheter, one can ascertain the effect of the intravascular lung on mixed venous arterial saturation. In the currently most advanced intravascular lung, the IVOX, its position in the vena cava unfortunately prohibits the passage or readjustment of the position of a pulmonary artery catheter with a fiberoptic capability.

A primary object of the invention is to develop and optimize a new configuration intravascular membrane lung which after percutaneous venous insertion will exchange the entire basal oxygen consumption and carbon dioxide production of an adult man or woman.

Another object of the invention is to provide such an apparatus which includes a multi-lumen catheter on which are mounted a plurality of gas exchange members in communication with the lumina of the catheter, tethered at one end to the catheter, and extending transversely of a longitudinal axis of the catheter to a distant free sealed end so that blood flowing in a direction generally parallel to the catheter is caused to flow across the gas exchange members. Still another object of the invention is to provide such an apparatus in which ventilating, or excessive flow of, oxygen is introduced via one lumen of the catheter and carbon dioxide diffused out of the blood is returned for disposal via another lumen of the catheter.

Yet another object of the invention is to provide a catheter with a selectively inflatable balloon at its distal end to propel the catheter and its gas exchange members to a desired final location in the body.

Yet a further object of the invention is to place the catheter and its gas exchange members in a location within the body to assure maximized oxygen delivery to the blood. This is achieved by placing the apparatus of the invention within the inferior vena cava, the right ventricle and the pulmonary artery.

Yet another object of the invention is to provide an intravascular membrane lung including an integral measurement catheter which can simultaneously assay the operation of the left and right heart without the need of inserting an additional catheter for that purpose.

Still other objects of the invention include the use of hollow, porous, polyethylene fibers as the gas exchange members, coating the device with heparin to minimize the risk of hemorrhage from the insertion sites, the use of optical fibers to readily determine the effect of the device on mixed venous oxygen saturation, sampling of the blood at the tip of the catheter, and heating of the oxygen to a temperature in the range of 2° C. and 5° C. warmer than the blood temperature.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

BRIEF DESCRIPTION OF THE DRAWINGS

FIG. 2 is a perspective view of an intravascular membrane lung intended for percutaneous venous insertion and embodying the present invention;

FIG. 3 is a perspective view, cut away and in section, of one component of the lung illustrated in FIG. 2;

FIG. 6 is a detail perspective view of another component of the artificial lung illustrated in FIG. 2;

FIG. 7 is a side elevation view of parts illustrated in FIG. 6;

FIG. 8 is a cross section view of parts illustrated in FIG. 6;

DETAILED DESCRIPTION OF THE PREFERRED EMBODIMENT

Figure 1:
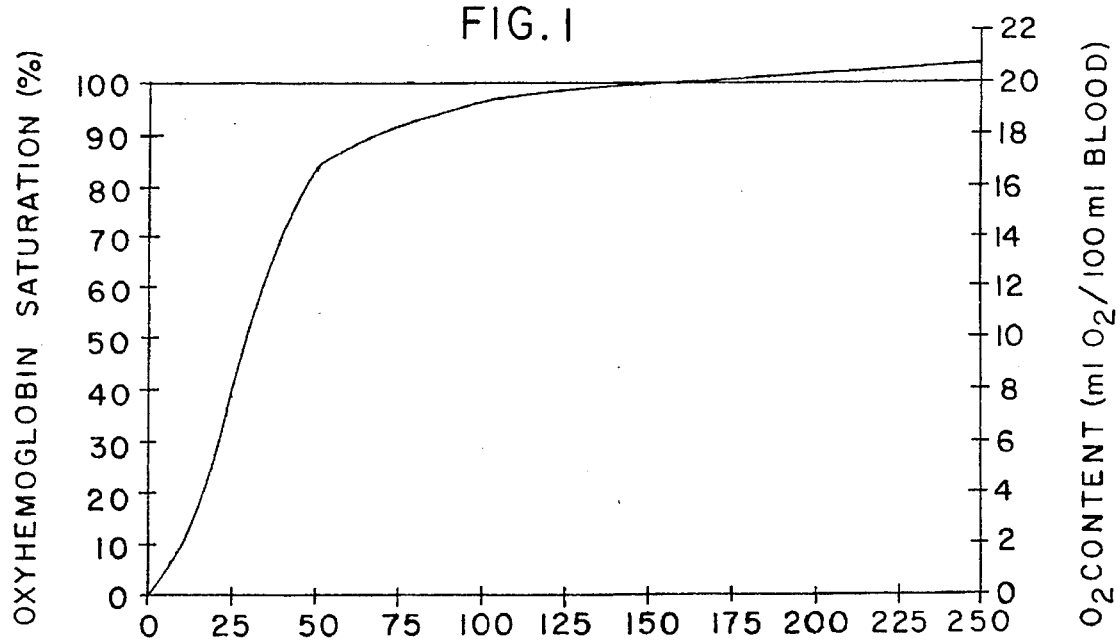
FIG. 1 is am oxygen dissociation curve which indicates the limit of the amount of oxygen which can be transferred into a given blood flow stream by an intravascular lung as a function of a constant inlet oxygen blood content.

Turn now to the drawings and, initially, to FIG. 2 which illustrates a new configuration intravascular membrane lung 20 embodying the present invention. The primary structural member of the lung 20 is an elongated multi-lumen catheter 22 which may be, for example, a commercially available diagnostic pulmonary artery catheter such as the OPTI-CATH® catheter manufactured and sold by Oximetrix, Inc. of Mountain View, Calif. The catheter 22 is more clearly illustrated in FIG. 3. It is of a flexible plastic material, preferably extruded polyvinyl chloride. Specifically, it is formed to include a ventilation, or gas inlet, conduit 24, a ventilation, or gas outlet, conduit 26, a balloon filling conduit 28, a blood sampling conduit 30, and optical fibers 32 which extend between its proximal end 34 and its distal end 36.

The catheter 22 may be of any suitable length and in a size appropriate to accommodate the gas exchange requirements of an adult human being. For this purpose, it may have an outer diameter of approximately 5.6 mm and a wall thickness of approximately 0.2 mm.

By way of the conduit 28, an inflatable balloon 38 at the distal end 36 of the catheter 22 can be selectively inflated between an ordinarily inactive solid line position and an inflated position as indicated by dotted lines in FIG. 2.

Figure 5:
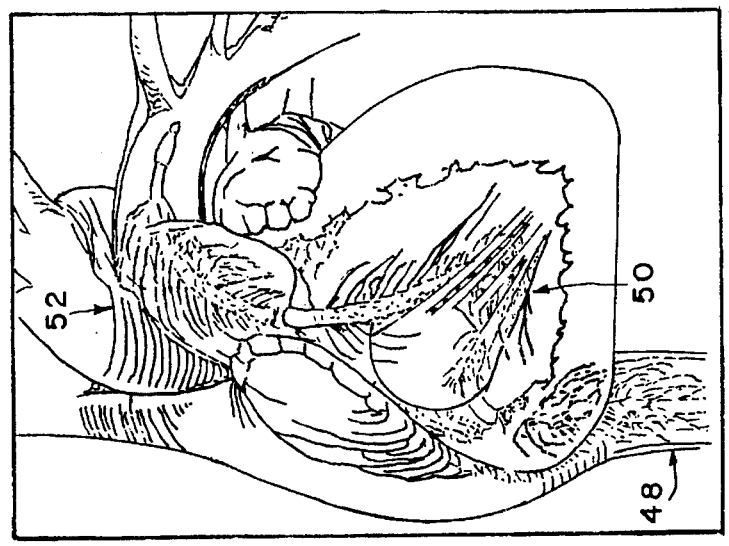
FIG. 5 is an enlarged view of a portion of FIG. 4.
Figure 4:
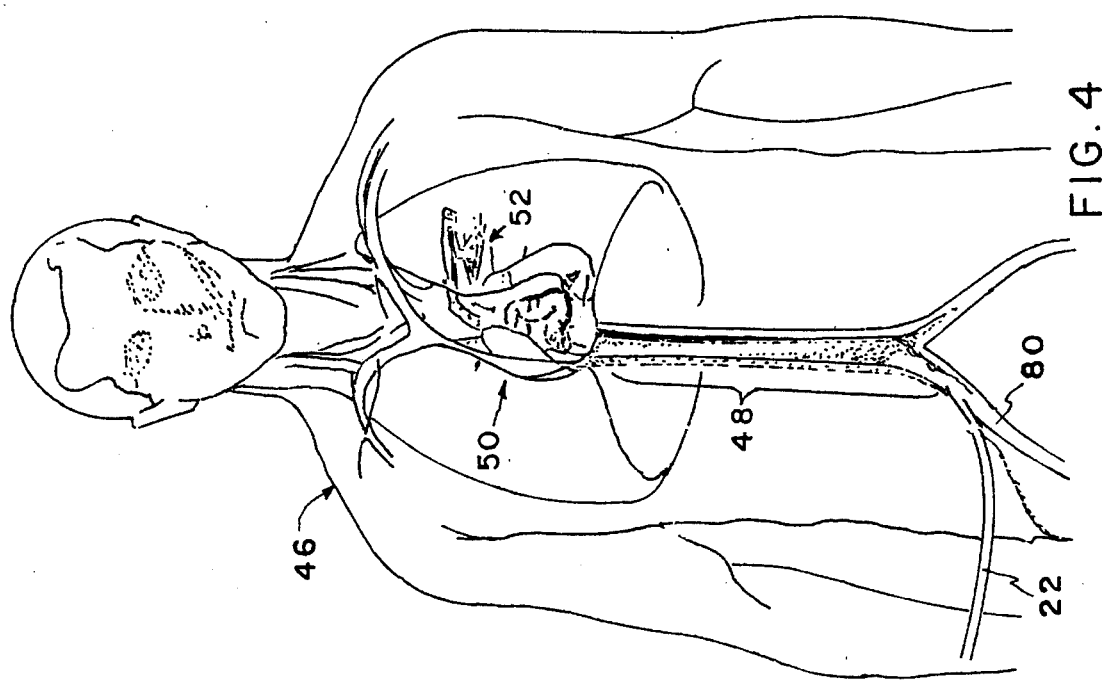
FIG. 4 is a front elevation view of a patient into whom the lung of the invention has been finally positioned.

With particular reference now to FIGS. 2, 4, and 5, the artificial lung 20 is provided with three distinct gas exchange regions 40, 42, and 44, respectively. When the lung 20 has finally assumed its operational position within a living body 46 as seen in FIG. 4 and in even greater detail in FIG. 5, the gas exchange region 40 of the lung 20 will be positioned within and substantially coextensive with the inferior vena cava 48, the gas exchange region 42 will be positioned within and substantially coextensive with the right ventricle 50, and the gas exchange region 44 will be positioned within and substantially coextensive with the pulmonary artery 52.

By so placing the artificial lung 20, it is able to effect gas exchange with venous blood draining from all of the tissues of the body thereby providing an excellent opportunity for exchanging the entire basal oxygen consumption and carbon dioxide production of the body.

At each of the gas exchange regions 40, 42, 44, there is a plurality of manifold sleeves 54 sealingly fixed to the catheter 22 at side-by-side spaced apart locations. As seen particularly well in FIG. 6, each of the manifold sleeves 54 overlies and contains a pair of apertures 56, 58 in the catheter 22. The apertures 56 are sized and positioned to communicate with the inlet conduit 24 while the apertures 58 are sized and positioned to communicate with the outlet conduit 26. Each manifold sleeve 54 is coaxial with the catheter 22, having a cylindrical wall 60 with an outer peripheral surface which is parallel to that of the outer surface of the catheter 22. In this manner, an annular space 62 is defined between the outer peripheral surface of the catheter and the cylindrical wall 60. Additionally, the cylindrical wall 60 is formed with a plurality of ports 64 (see FIGS. 6, 7, and 8) which extend therethrough at a large number of longitudinally and circumferentially spaced locations.

A pair of perforated end caps 66, 68 positioned in spaced parallel planes are sealingly attached to the catheter 22 and to the cylindrical wall 60. Epoxy or other suitable adhesive may be employed for this purpose.

The components of the manifold sleeves 54 are preferably composed of polycarbonate because of its ease of machining, moderate thromboresistance and its ability to be coated with heparin via the CARMEDA® process. Other suitable materials are within the scope of the invention, however. In a typical construction, the outer diameter of each manifold would be 7 mm and the annular space 62 would typically have a transverse dimension of 0.2 mm. In like manner, the ports 64 would have a diameter of approximately 0.4 mm.

As seen particularly well in FIGS. 6, 7, and 8, hollow polypropylene fibers 70 whose generally cylindrical walls are microporous membranes and which may nominally have a wall thickness of approximately 50 microns and an outside diameter of 280 microns are bonded to the cylindrical wall 60 at each of the ports 64 by using biomedical grade epoxy or in some other suitable fashion. In this instance, the ports 64 may have a diameter of approximately 400 microns. The fibers just noted represent one of a large number of choices available for medical gas exchange purposes. After bonding to the cylindrical wall 60, each hollow fiber 70 is sealed with epoxy at its free tip end 72.

The fibers 70 may assume a perpendicular relationship with the catheter 22 as seen in FIG. 8 or they may assume some other angular relationship, for example, swept in a direction away from that of insertion into the body as illustrated in FIG. 7. Of course, if the fibers are perpendicular to the longitudinal axis of the catheter 22, the total width of the artificial lung 20 will be greater than fibers of the same length being swept back. The actual shape of the artificial lung 20 free floating in the vasculature will depend upon the angle at which the fibers are mounted to their associated manifolds 54. Their shape during insertion and removal from the body will be that of a cylinder as the fibers fold in to conform to the shape of the introduction cannula to be described.

As previously mentioned, the relatively poor gas exchange performance of existing intravascular lungs has led the inventors to consider other ways of replacing oxygen flushed microporus fibers in better positions to oxygenate and decarbonate venous blood. Tethering fibers to both ends of a gas delivery catheter constrains much of the surface area of the fiber to be parallel to the direction of the returning venous blood. This is not an optimal positioning for gas transfer. This has led the inventors to conceive of a diffusion based intravascular lung having the construction of the invention. In the instance of the invention, only one end of each hollow fiber 70 is sealed (see especially FIG. 8) and it is allowed to float freely in the blood stream. The attached ends of the hollow fibers open transversely into the annular space 62 between the cylindrical wall 60 and the catheter 22 which is flushed by fresh gas, notably pure oxygen, as indicated by arrow 74 entering via aperture 58. The free fiber 70 can float so that its whole length lies transversely of the passing blood stream as indicated by an arrow 76, a much more favorable positioning for gas exchange than provided by known devices. The incoming oxygen diffuses down the lumen of each hollow fiber 70 and then across the microporus membrane into the blood stream as represented by the arrow 76. After carbon dioxide leaves the blood and crosses the microporus membrane by diffusion, it must then diffuse along the fiber axis until it enters the outlet conduit 26 via the annular space 62 and aperture 56, where it is swept away by the flowing stream of excess fresh oxygen supplied from outside of the patient's body.

Each manifold is approximately 1 cm in length and the spacing between adjacent manifold sleeves 54 along the length of the catheter 22 is approximately 1 cm. A sufficient number of manifold sleeves with hollow fibers 70 thereon are provided to define the respective gas exchange regions 40, 42, and 44 such that the region 40 is substantially coextensive with the inferior vena cava, the region 42 is substantially coextensive with the right ventricle, and the region 44 is substantially coextensive with the pulmonary artery 52. In each of these regions, it may be desirable to adjust the lengths of the hollow fibers 70 to conform generally to the diameter of the particular cavity which they are placed. While fibers having a nominal length of approximately 0.4 cm are considered to be desirable, this length may vary considerably.

Figure 9A:
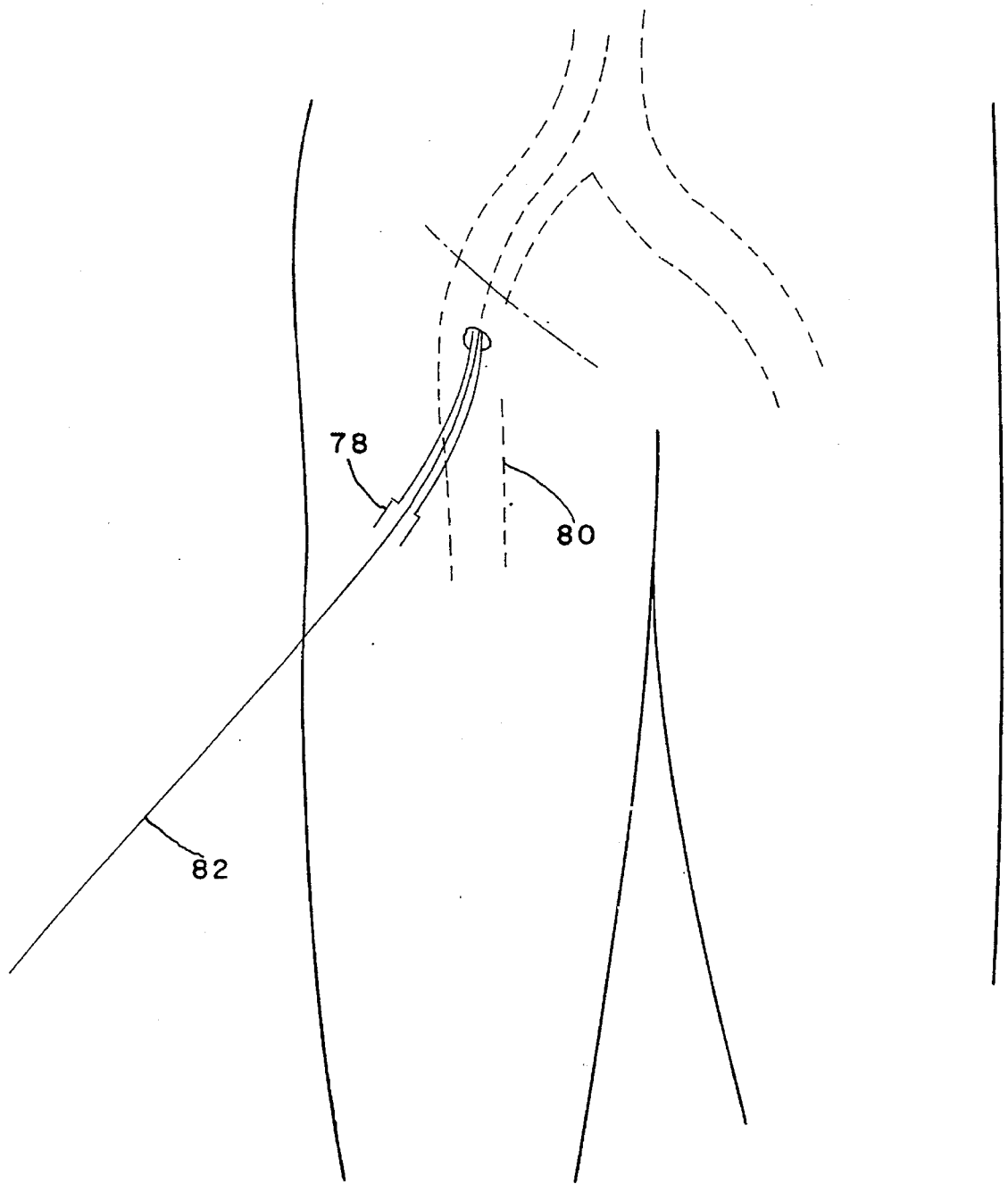
FIGS. 9A through 9F illustrate a series of successive steps in the procedure of inserting the artificial lung of the invention into a human body.
Figure 9B:
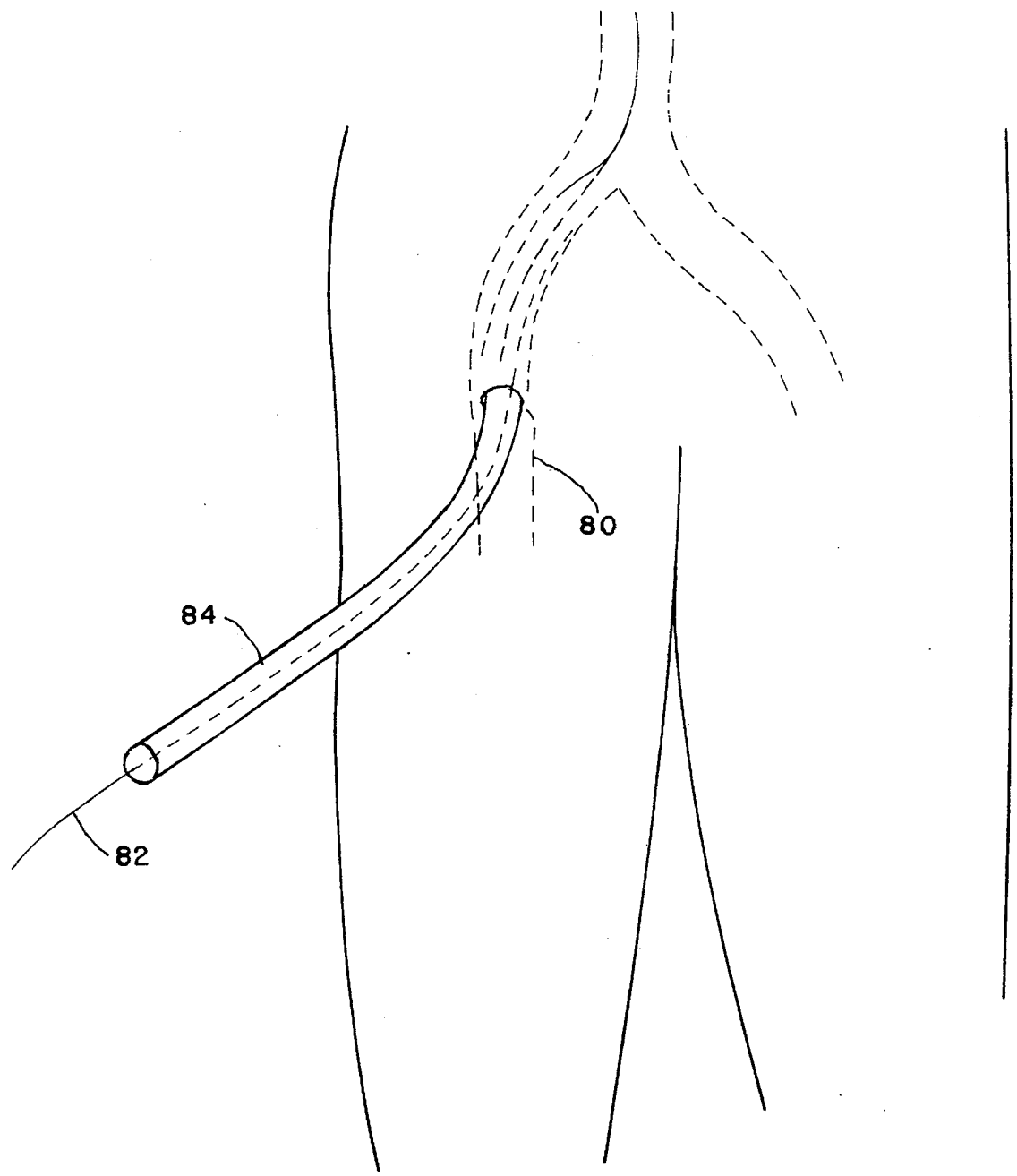
Figure 9C:
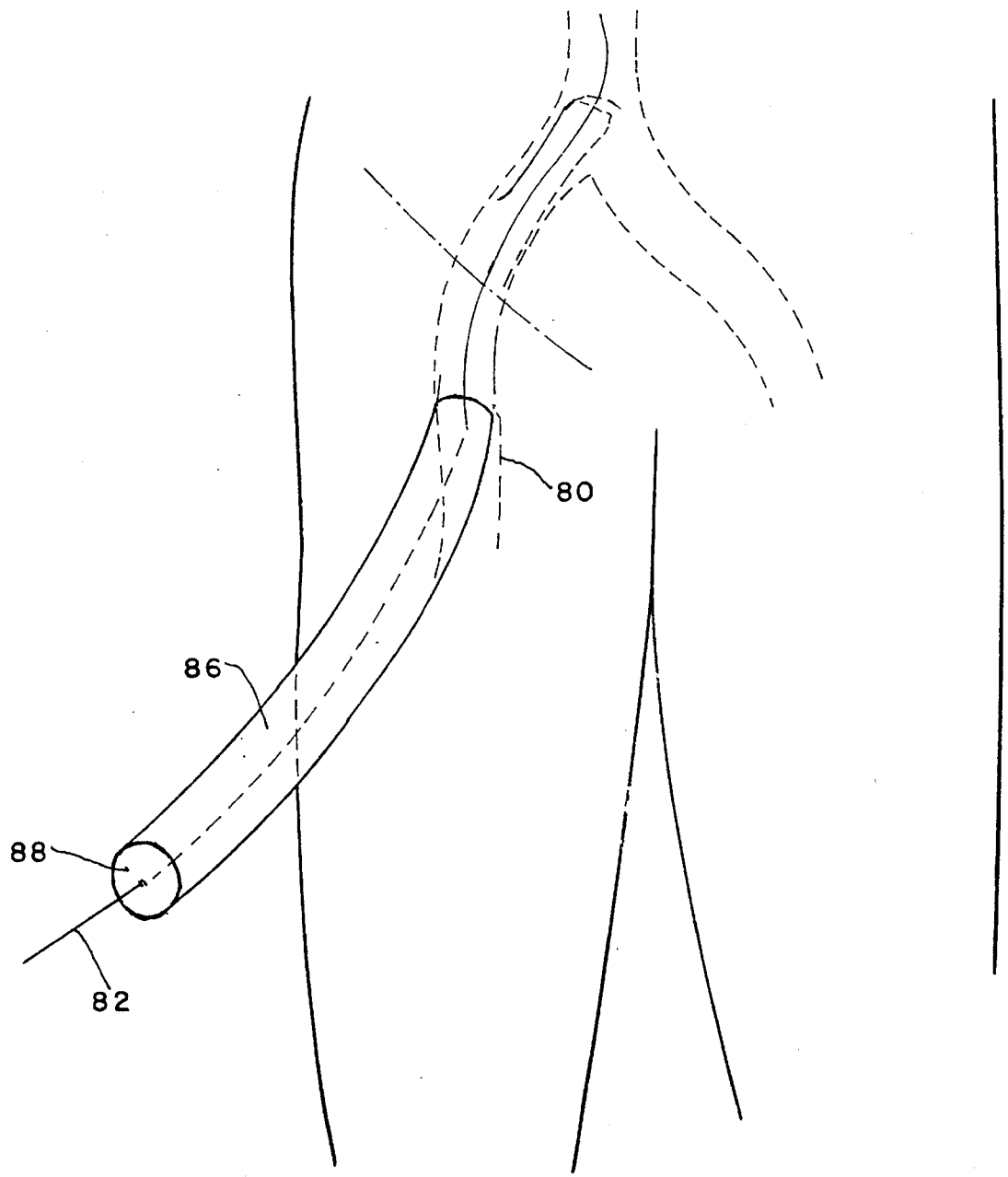
Figure 9D:
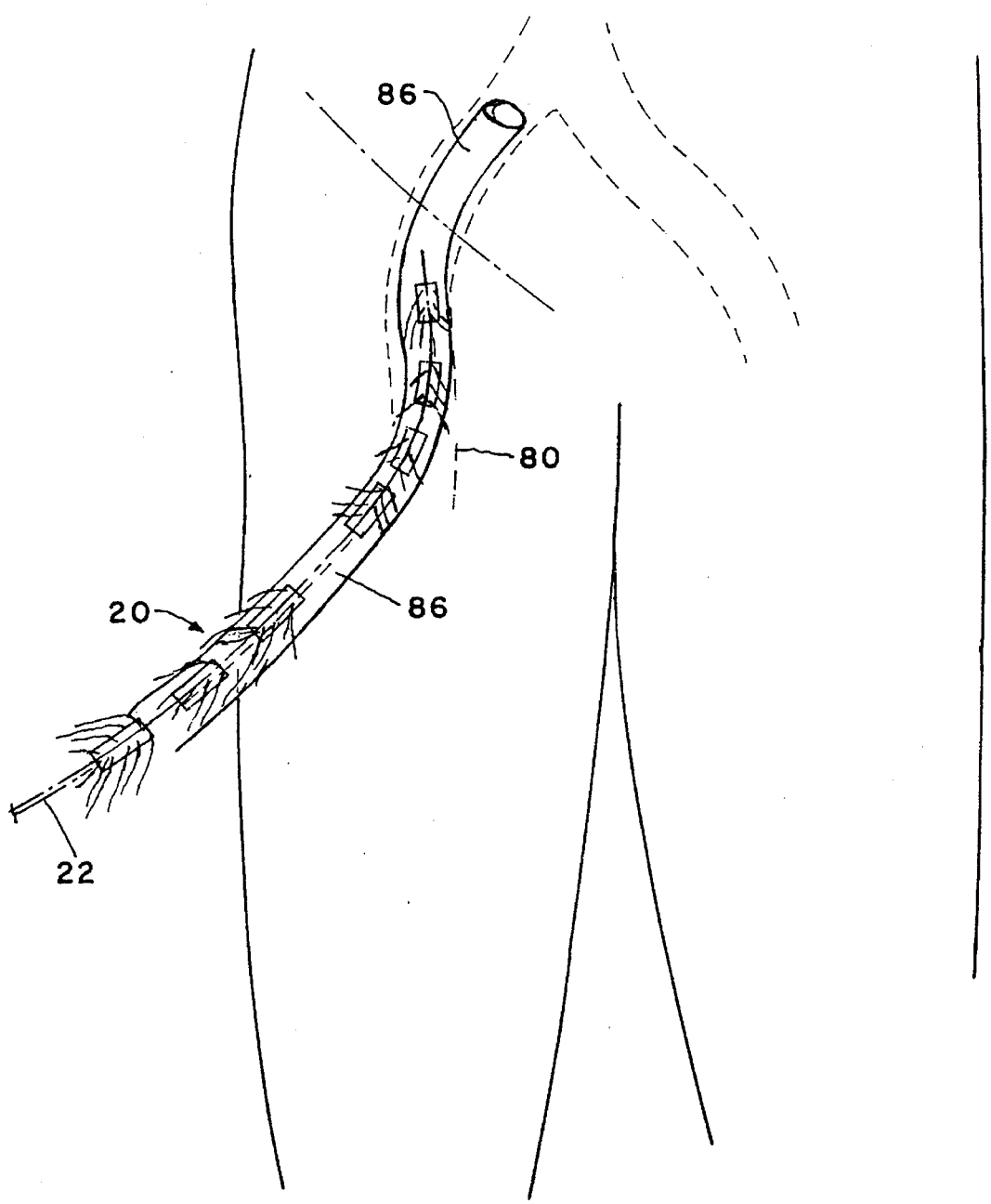
Figure 9E:
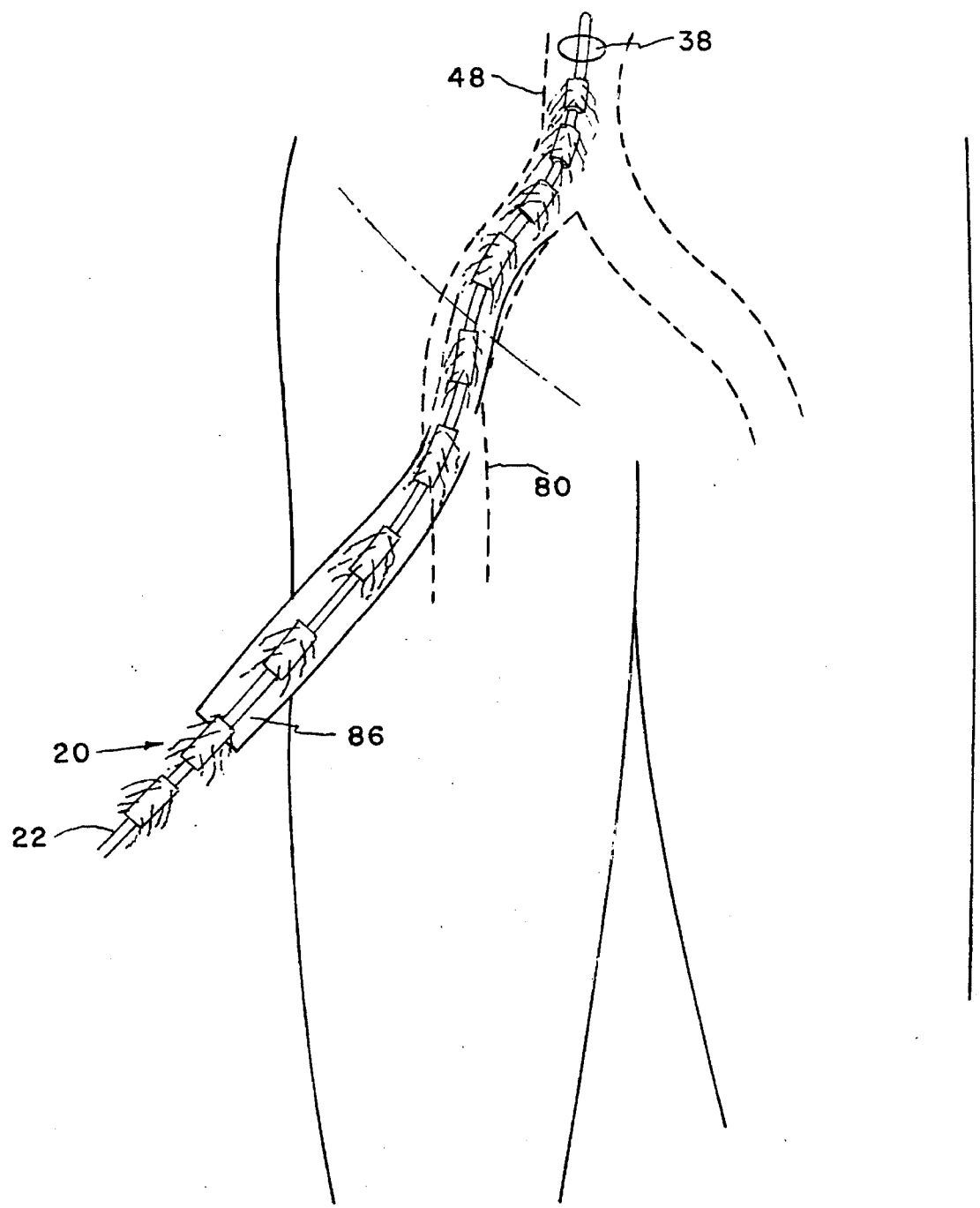

As was noted previously, the artificial lung 20 is intended to be inserted and removed percutaneously without need for surgery. Turn now, with particular attention, to FIGS. 4, 5, and 9A–9F. Insertion of the artificial lung is intended to follow the Seldinger technique in which a narrow gauge needle 78 (FIG. 9A) is used to locate the lumen of the femoral vein 80. Then a guide wire 82 is passed through the finder needle 78 into the femoral vein whereupon the finder needle is removed. A flexible dilator 84 (FIG. 9B) is then passed over the guide wire 82 and into the femoral vein 80 to enlarge the entrance hole. Thereupon, viewing FIG. 9C, an introducer sheath 86 with obturator 88 is placed over the guide wire 82 and into the vein 80. When insertion of the artificial lung 20 into the body is desired, the obturator 88 is removed and the distal end 36 of the artificial lung 20 is inserted into the introducer sheath 86, then advanced manually into the femoral vein 80 (FIG. 9D). Once inserted into the vein, the balloon 38 is inflated (FIG. 9E).

In the standard operational manner, the diameter of the balloon, while substantially larger than that of the catheter 22 and of the manifold sleeves 54 thereon, is sufficiently smaller than the diameter of the vein 80 and of the other internal cavities into which the artificial lung 20 is to advance to assure that it will not become undesirably lodged before reaching its destination. In any event, the size of the balloon can be altered by the attendant if necessary.

Figure 9F:
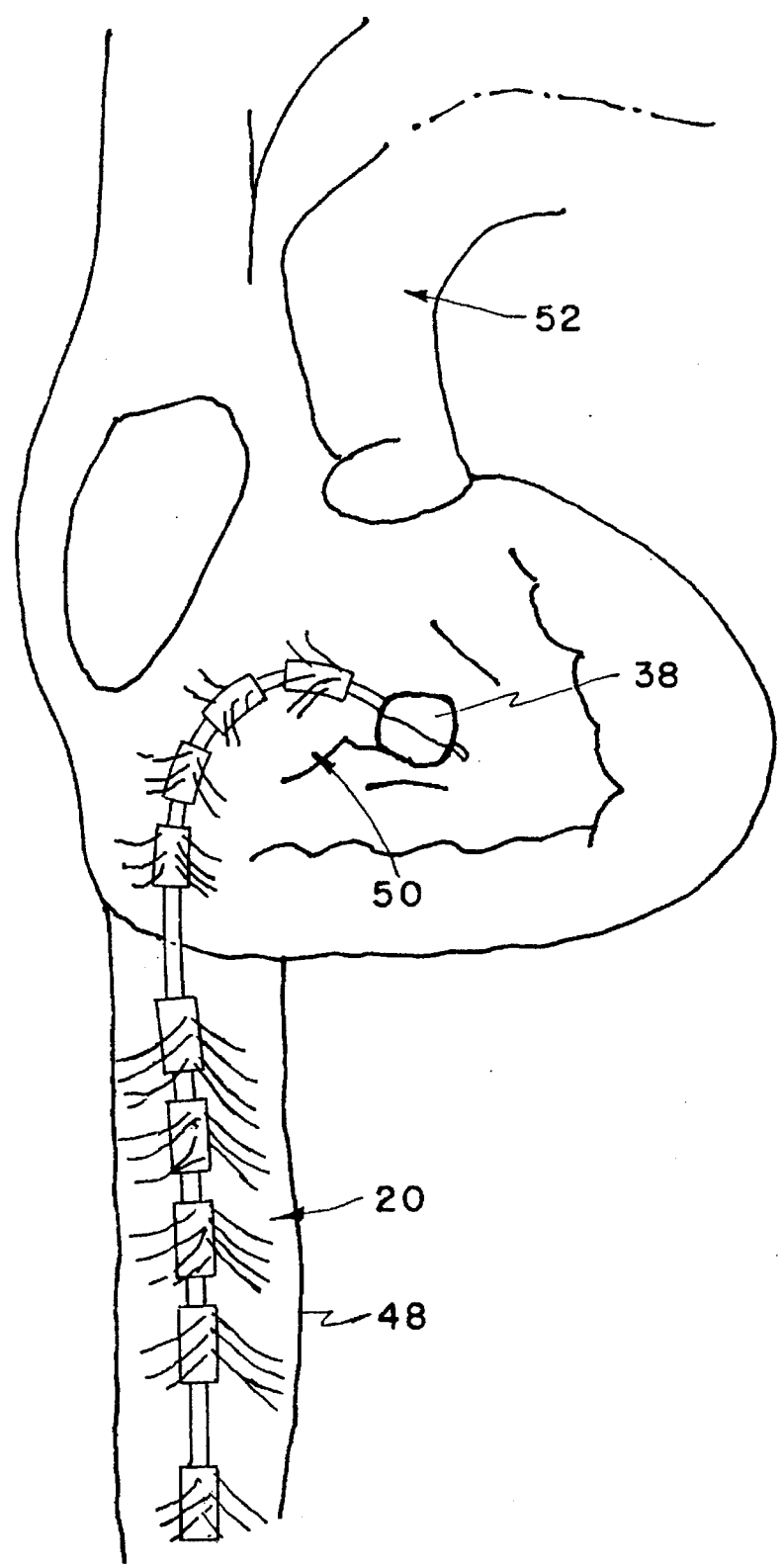

Blood flow propels the balloon 38 and its trailing appendage along and through the inferior vena cava 48, the right ventricle 50, and the pulmonary artery 52 (FIGS. 9F, 4, and 5). Movement of the balloon and of the artificial lung 20 is observed by fluoroscopy. If any difficulties are encountered, the device can be withdrawn to a greater or lesser extent, as necessary, by the attendant acting on the proximal end 34 of the artificial lung 20. When the balloon 38 reaches a position such that the gas exchange region 40 is placed generally within and substantially coterminous with the inferior vena cava, the gas exchange region 42 is placed generally within and substantially coterminous with the right ventricle, and the gas exchange region 44 is placed generally within and substantially coterminous with the pulmonary artery, the proximal end 34 is suitably anchored to the skin of the patient preventing further relative movement between the lung 20 along the cavities of the body in which it is placed. Subsequent removal of the lung 20 simply entails sliding it out of the femoral vessel. While removal will cause bending and possibly kinking of the hollow fibers 70, they should not be caused to break and should be sufficiently malleable to avoid tissue damage during the extraction procedure.

It was earlier mentioned that studies have offered evidence to the effect that condensation of water vapor, which is transferred across the fibers 70 from the liquid to the gas phase within the lumens of the microporous fibers, may draw blood plasma across the fibers by capillary action, thereby gradually reducing gas transfer. However, by warming the gas to the blood temperature, plasma leakage is prevented and gas transfer remains constant over an extended period of time. Accordingly, it is highly desirable to employ, in association with the artificial lung 20, a gas temperature control system as part of a computerized automated control system 90 depicted in FIG. 10. The algorithm for maintaining the proper gas temperature in the artificial lung 20 is shown in FIG. 11. The aim of the algorithm is to find and maintain an inlet gas temperature ($T_{maintain}$) that will keep the outlet gas temperature 2° C. ($T_{min}$) warmer than the blood temperature, but not more than 5° C. warmer ($T_{max}$). The minimum inlet gas temperature that will damage the blood, body tissue, or artificial lung 20 is defined as $T_{danger}$. The inlet gas is never to be heated above this temperature. Delay is defined as the time that it takes to measure a temperature difference at an outlet gas thermometer due to a change in temperature of the inlet gas. As the algorithm begins, the gas flow is off. The gas warmer is warmed up to $T_{maintain}$ and then the gas flow is slowly increased until the desired gas flow is reached.

Figure 10:
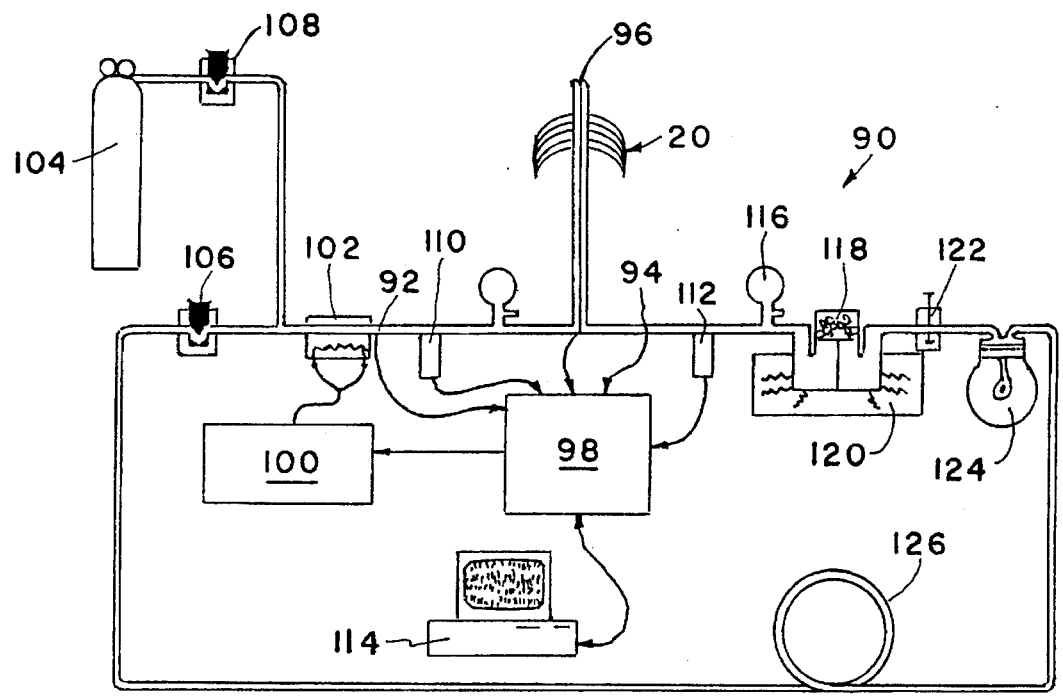
FIG. 10 is a diagrammatic view of a control system for operating the artificial lung of the invention.
Figure 11:
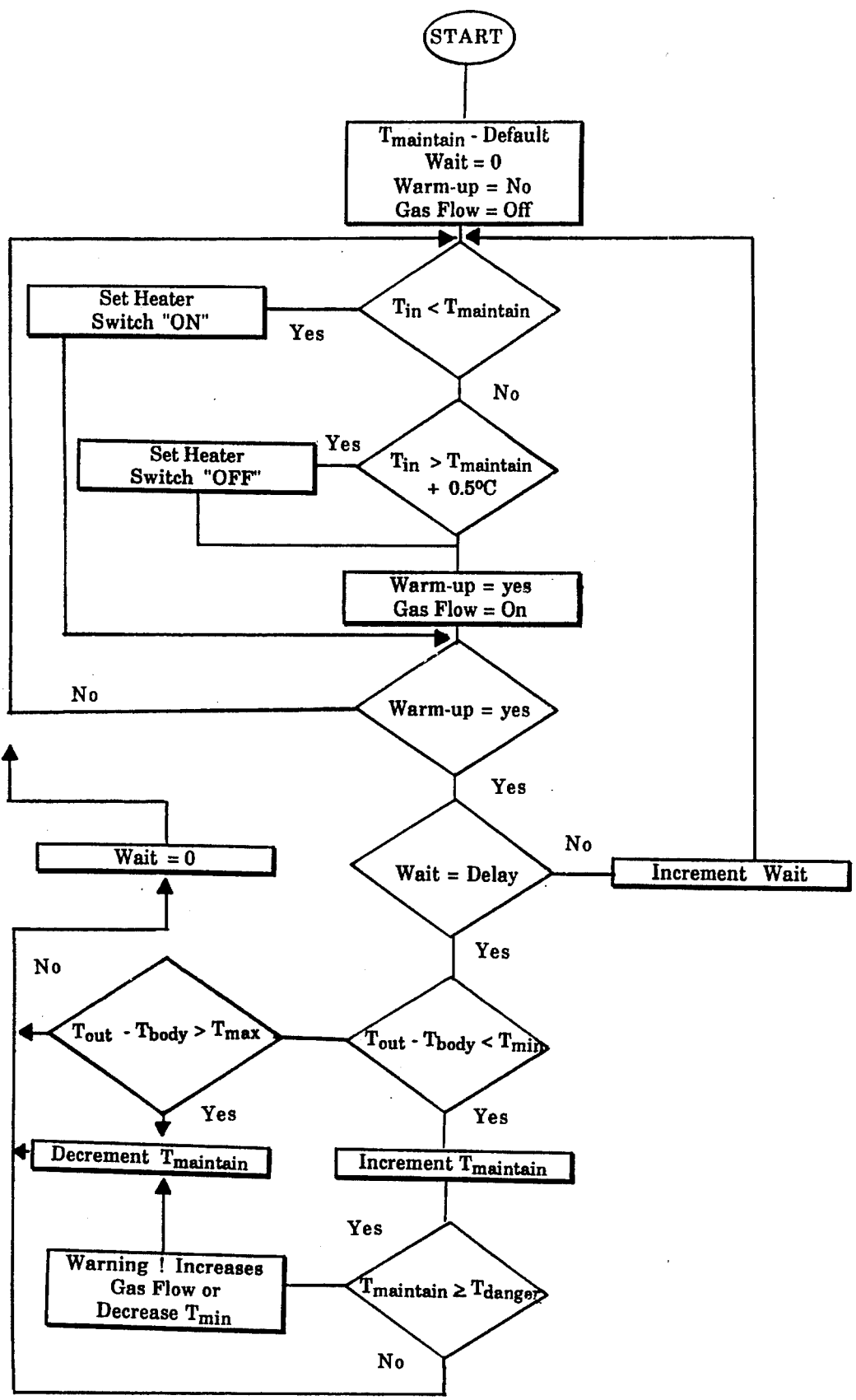
FIG. 11 is a flow chart depicting the operation of a part of the control system depicted in FIG. 10.

In the system 90, thermocouple transducers 92, 94, and 96 measure and record, respectively, $T_{in}$, $T_{out}$ and $T_{blood}$ (FIG. 10). A data acquisition system 98 then sends control signals to a heater control box 100 which operates a heater element 102.

By reason of the control system 90, a patient could be maintained on the artificial lung 20 for a duration of 12 to 24 hours using a single "E" size oxygen cylinder 104 at a gas flow rate of approximately 2 to 4 l./min. Because the system is a closed one, transportation of the patient is made practical. In the system 90, a mass flow controller 106 serves to maintain a constant mass flow through the artificial lung 20. A second mass flow controller 108 connected to the oxygen cylinder 104 serves to feed oxygen into the system at a rate required to maintain a constant inlet pressure. The inlet and outlet pressures are monitored, respectively, by transducers 110, 112, that connect to the data acquisition system 98 and to a computer 114. From the outlet of the catheter 22, the gas flows past a vacuum gauge and vacuum pop-off valve 116 to prevent a vacuum strong enough to collapse the gas conduits. A $CO_2$ absorber 118 serves to remove the $CO_2$ from the outlet gas to be recirculated. The gas then flows through a thermoelectric cooler 120 that removes water vapor from the outlet gas. Finally, the gas passes through a needle valve 122 used to regulate the flow and into a vacuum pump 124 from which it is expelled into the procedure room. The automated temperature control system described above is used to warm and cool the circulating gas. A warming loop 126 returns the gas to room temperature following its flow through the cooler 120 to reduce the energy requirement of the gas warmer, although the vacuum pump 124 utilized by the system may provide enough heat to make this unnecessary.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A method of implanting in a living body an intravascular membrane lung by way of percutaneous insertion into cavities of the body through which blood flows in series including a femoral vein, an inferior vena cava, a right ventricle, a pulmonary artery, and natural lungs, said method comprising the steps of:

(a) inserting percutaneously into the femoral vein a distal end of an elongated catheter having a longitudinal axis and first and second conduits therethrough, and including a plurality of elongated hollow flexible microporous gas exchange fibers having outer surfaces, said fibers tethered only at one end to the catheter and in communication with the first and second conduits and extending transversely of the longitudinal axis of the catheter;

(b) advancing the catheter into and through the femoral vein until the gas exchange fibers extend transversely of the catheter and are positioned within and substantially coextensive with the pulmonary artery, within and substantially coextensive with the right ventricle, and within and substantially coextensive with the inferior vena cava;

(c) delivering oxygen through the first conduit of the catheter to the gas exchange means and thence to the blood flowing across the gas exchange means; and (d) removing carbon dioxide from the blood flowing across the gas exchange means, through the gas exchange means, then through the second conduit of the catheter.

2. A method as set forth in claim 1 wherein the catheter has an external nominal dimension;

wherein each of the body cavities has an inner nominal dimension;

and wherein step (b) includes the step of:

(e) inflating a balloon attached to a distal end of the catheter and having an enlarged size larger than a nominal transverse dimension of the catheter and smaller than the inner nominal dimensions of any of the body cavities into which it extends whereby blood flowing back to the natural lungs of the body will propel the catheter with its plurality of microporous fibers into and through the inferior vena cava, into and through the right ventricle, and into and through the pulmonary artery.

3. A method as set forth in claim 1 wherein step (c) includes the steps of:

(f) delivering an amount of oxygen through the catheter to the gas exchange fibers which is in excess of that needed to fully oxygenate the blood passing across the gas exchange fibers; and wherein step (d) includes the steps of:

(g) allowing $CO_2$ in the blood to leave the blood and enter the microporous fibers by diffusion, then diffuse along the length of the microporous fibers to the second conduit of the catheter and (h) withdrawing the $Co_2$ and the excessive oxygen for disposal via the second conduit of the catheter.

4. A method as set forth in claim 1 including the step of:

(i) withdrawing blood samples from the distal end of the catheter for electrometric and spectrophotometric measurement thereof.

5. A method as set forth in claim 1 including the step of:

(i) fiberoptically monitoring oxygenation of the blood passing over the gas exchange fibers.

6. A method as set forth in claim 1 including the step of:

(i) heparin coating the outer surfaces of the gas exchange fibers for minimizing the risk of hemorrhage at the location of insertion of the catheter into the living body.

7. A method as set forth in claim 1 wherein step (c) includes the steps of:

(i) measuring the temperature of the blood in the living body; and (j) heating the oxygen immediately prior to delivery thereof to the catheter to a temperature in the range of approximately 2° C. to 5° C. above the temperature of the blood.

* * * * *